(12) United States Patent
Marwah et al.

(10) Patent No.: US 6,274,746 B1
(45) Date of Patent: Aug. 14, 2001

(54) PROCESS FOR ALLYLIC OXIDATION USING METAL HYPOCHLORITE AND ALKYL HYDROPEROXIDE

(76) Inventors: Padma Marwah, 6710 Spring Grove Ct., Middleton, WI (US) 53562; Henry A. Lardy, 1829 Thorstrand Rd., Madison, WI (US) 53705; Ashok Kumar Marwah, 6710 Spring Grove Ct., Middleton, WI (US) 53562

( * ) Notice: Subject to any disclaimer, the term of this patent is extended or adjusted under 35 U.S.C. 154(b) by 0 days.

(21) Appl. No.: 09/651,604

(22) Filed: Aug. 30, 2000

(51) Int. Cl.[7] .................................. C07J 1/00; C07J 9/00
(52) U.S. Cl. ............................................. 552/542; 552/615
(58) Field of Search ....................... 552/615, 542

(56) References Cited

U.S. PATENT DOCUMENTS 5,100,460 * 3/1992 Desbordes et al. ................ 71/94
5,869,709 * 2/1999 Marwah et al. .................. 552/615

OTHER PUBLICATIONS

Lu et al., Fenzi Cuihua, vol. 8(2), pp. 143–146, 1994.*
Fieser's Reagents in Organic Synthesis John Wiley & Sons, N.Y. 1 1084 (1967); 4 456 (1974); 5 617 (1975); 6 543 (1977) 7 337 (1979); 8 461 (1980); 9 430 (1981); 10 365 (1982); 11 107 & 487 (1984); 15 293 (1990); 16 308 (1992); 17 316 (1994); 18 84 & 335 (1999); and 19 313 (1999).
Encyclopedia of Reagents in Organic Syn. Ed. Leo A. Paquette, John Wiley & Sons NY (1995) 966–68 & 4580–86.
Skarzewski J. & Siedlecka R.; Organic Preparation & Procedures Int. 24 (1992) p. 623–647.

* cited by examiner

Primary Examiner—Barbara P. Badio

(57) ABSTRACT

The present invention is directed to a process for effecting the allylic oxidation of an allylic compound having at least two allylic hydrogen atoms on the same carbon atom into corresponding α,β-unsaturated carbonyl compound, using a combination of a metal hypochlorite and an alkyl hydroperoxide in a mixture of suitable conventional organic solvent(s) and/or water at a temperature of between about −5° C. to +25° C.

20 Claims, No Drawings

PROCESS FOR ALLYLIC OXIDATION USING METAL HYPOCHLORITE AND ALKYL HYDROPEROXIDE

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

This invention relates to a simple, and inexpensive way to allylically oxidize organic compounds having methylene groups activated by adjacent olefinic double bonds to $\alpha,\beta$-unsaturated carbonyl compounds, utilizing a metal hypochlorite and an alkyl hydroperoxide. The process provides a good example of green chemistry; the aqueous waste generated is non-toxic.

BACKGROUND OF THE INVENTION

Allylic oxidation of compounds bearing active methylene groups to corresponding $\alpha,\beta$-unsaturated carbonyl compounds is an important organic reaction having applications in a variety of fields ranging from agricultural products to pharmaceuticals and the like. Allylic oxidation reactions have traditionally been performed using a wide variety of chromium(VI) compounds. Among other common oxidants are potassium permanganate, manganese dioxide, ruthenium compounds, selenium dioxide, copper and its compounds. Catalytic oxidation using oxygen or air is known whereby metal compounds and N-hydroxy cyclic imides have been used as catalysts. Most of these procedures are not environmentally friendly, and typically suffer from one or more additional drawbacks such as unsatisfactory yields, use of large excess of the oxidant(s), harsh reaction conditions, use of toxic chemicals, difficulty in scaling up, generation of copious amount of toxic waste, use of expensive reagents etc. and therefore, are not industrially feasible processes for bulk production.

The use of tert-butyl hydroperoxide in combination with some of the oxidants such as chromium, ruthenium, and copper compounds has afforded allylically oxidized product (s) under relatively milder conditions but the reaction still utilizes the toxic metal compounds, and/or often requires use of toxic solvents such as benzene and the process produces toxic waste making the process eco unfriendly. Also, because of the incomplete and/or partial conversion, the product is often contaminated with the starting material and, quite often, complex mixture of products comprised of alcohols, ketones, hydroperoxides etc. is obtained.

Hence, a continuing need exists for a simple, efficient and cost effective as well as eco-friendly procedure for selectively effecting the allylic oxidation of organic compounds bearing an active methylene group, particularly $\Delta^5$-steroids into corresponding $\alpha,\beta$-unsaturated ketones.

In our previous patent (Marwah et al, U.S. Pat. No. 5,869,709) we have described a new cost effective, simple procedure for allylic oxidation of a wide variety of organic compounds, utilizing sodium periodate or periodic acid and aqueous tert-butyl hydroperoxide. The procedure was developed successfully and is being utilized for the industrial production of one of our commercial products. However during commercial production it was observed that the only drawback associated with this process was production of large amount of aqueous waste containing salts of various lower oxidation stages of iodine such as iodates, iodides etc.

The present patent deals with a simple, eco-friendly, cost effective procedure based on green chemistry to the extent feasible, for the allylic oxidation of a wide variety of organic compounds having at least two allylic hydrogens into corresponding $\alpha,\beta$-unsaturated carbonyl compounds.

Sodium hypochlorite is a well-known oxidizing agent and a household bleaching agent and disinfectant and is easily and cheaply available under various brand names such as clorox. The commercially available aqueous solution of sodium hypochlorite comes with ~5.0–12.5% available oxidant (w/v, ~0.7 M–1.75 M). Concentration is expressed as % available chlorine since half the chlorine in bleach is present as sodium chloride. In the chemical synthesis, sodium and calcium hypochlorite have been successfully used to oxidize aldehydes into corresponding acids (—CHO into COOH) preferably in presence of a phase transfer catalyst, and secondary alcohols into ketones (—CHOH into —C=O) in presence of acetic acid, and primary alcohols to esters, ethers to esters, and thioethers to sulfoxides. Hypochlorites are effective, although infrequently utilized reagents for epoxidation of enones and polycyclic arenes. They are also reagents for N-chlorination, oxidative coupling, degradation reactions etc. and reactive methylene groups have occasionally been oxidized to the corresponding gem-diols. (Encyclopedia of reagents for organic synthesis; Editor-in-Chief: Leo A, Paquette, John Wiley & Sons 1995, p.966–68, 4580–86; Skarzewski J. and Siedlecka R., Organic Preparation and Procedures International, 24 (1992) 623–647 and Fieser's Reagent in Organic Synthesis, John Wiley & Sons, 1 1084 (1967); 4 456 (1974); 5 617 (1975); 6 543 (1977); 7 337 (1979); 8 461 (1980); 9 430 (1981); 10 365 (1982); 11 107 & 487 (1984); 15 293 (1990); 16 308 (1992); 17 316 (1994); 18 84 & 335 (1999); and 19 313 (1999)). It has also been reported that a methylene or methyl group attached to an aromatic ring can be oxidized to carboxylic acids provided the ring contains also an acetyl group. (Fieser's Reagent in Organic Synthesis 1, 1084) However, to the best of our knowledge, metal hypochlorites have never been used for a one step allylic oxidation of allylically activated methylene group to corresponding $\alpha,\beta$-unsaturated carbonyl compound (>$CH_2$ into >C=O).

BRIEF SUMMARY OF THE INVENTION

The present invention is concerned with a new green process for the allylic oxidation of organic compounds having at least two allylic hydrogen atoms on the same carbon atom. It is a simple, efficient, cost effective and eco friendly procedure, which generates non-toxic aqueous wastes in minimum possible amount. The present invention is the result of an extensive investigation to discover a process for allylic oxidation involving the use of so called green chemistry to the extent possible. The procedure involves reactively contacting a suitable organic compound with a combination of a metal hypochlorite and an alkyl hydroperoxide under conditions sufficient to effect oxidation of the allylic hydrogens on the organic compound to give corresponding $\alpha,\beta$-unsaturated carbonyl compound.

DETAILED DESCRIPTION OF THE INVENTION

The present process is extremely cost effective and useful both in terms of yield and operational simplicity. It is particularly good for the allylic oxidation of $\Delta^5$-steroids and benzylic compounds. Good to excellent yields are obtained with low molar ratios of the reactants at sub ambient or near ambient reaction temperatures. A characteristic feature of the present invention is that it is an example of green chemistry to the extent feasible since it generates non-toxic aqueous waste materials in minimum possible amount.

The process of the present invention comprises allylically oxidizing an organic compound having at least two allylic hydrogen atoms on the same carbon atom into corresponding $\alpha,\beta$-unsaturated carbonyl compound.

The term "allylic oxidation" embraces, in the scope of the present invention, oxidation of an allylic compound by replacing two allylic hydrogens with oxygen, wherein the term "allylic compound" signifies in the scope of the present invention any organic compound incorporating the structure $>C_a=C_b-C_cH_n$ within the molecule, wherein n is 2 or 3.

The term "benzylic compound" as defined in the scope of the present invention refers to an aromatic compound having a $-CH_n$(n=2 or 3) group directly attached to an aromatic ring.

As utilized herein, including the claims, the term "reactants" collectively refers to allylic substrates, metal hypochlorite and alkyl hydroperoxide. Solvents, including both aqueous and organic solvents, are specifically excluded from the definition of reactants.

The term "inert organic solvent" as defined in the scope of the present invention refers to organic solvent(s) or mixture thereof which do not react with reactants under the experimental conditions as disclosed in the present invention.

According to the inventive process an allylic compound is reacted with a metal hypochlorite and an alkyl hydroperoxide under conditions sufficient to effect oxidation of allylic hydrogen atoms on the organic compound. For example, the compound having at least two allylic hydrogen atoms on the same carbon atom, can be allylically oxidized to corresponding $\alpha,\beta$-unsaturated carbonyl compounds by (i) dissolving the substrate in a water immiscible organic solvent or a water miscible organic solvent and/or tert-butyl hydroperoxide, (ii) adding a hypochlorite oxidant such as aqueous sodium hypochlorite slowly with continuous stirring at ambient to below ambient temperature.

The term allylic compound includes any organic compound as defined above having at least two allylic hydrogen atoms on the same carbon atom. Exemplary allylic compounds include specifically, but not exclusively, (i) steroids and steroids, such as androstenes, cholesterol, estraenes, pregnenes and derivatives thereof such as alcohols, esters, ethers, ketals etc. (ii) aromatic benzylic compounds such as fluorene, acenaphthene, diphenyl methane and the like, (iii) isoprenoids, such as, carotenoids, terpenes, sesquiterpenes and vitamins, and (iv) aliphatic vinylic compounds having at least two allylic hydrogen atoms such as unsaturated fatty acids and their esters.

Preferred starting materials in the process of present invention are the steroids having at least two allylic hydrogen atoms on the same carbon atom, more particularly $\Delta^4$- and $\Delta^5$-steroids such as testosterone, dehydroepiandrosterone, cholesterol and derivatives thereof, because such steroids possess pharmacological activity and can be conveniently and effectively allylically oxidized by the process of the present invention.

An oxidant system of a metal hypochlorite and an alkyl hydroperoxide is used to allylically oxidize the allylic compound. The term metal hypochlorite as used in the scope of the present invention references monovalent alkali metal hypochlorite such as sodium hypochlorite or divalent metal hypochlorite such as calcium hypochlorite. The preferred hypochlorite is aqueous sodium hypochlorite. Aqueous sodium hypochlorite is easily available and is commercially sold as household bleach or laundry bleach. The aqueous sodium hypochlorite oxidant is usually supplied as ~5.0%–12.5% available chlorine (w/v, ~7 M–1.75 M) and is used as such. The pH of commercial bleach is typically 11–12.5, but can be adjusted and buffered to some extent. Alkaline earth metal hypochlorite e.g. calcium hypochlorite is available from a number of chemical suppliers as solid and can be used as such. The term alkyl hydroperoxide as used in the scope of the present invention references an alkyl hydroperoxide wherein alkyl group is derived from upto eight carbon atoms. The preferred alkyl hydroperoxide is tert-butyl hydroperoxide. tert-Butyl hydroperoxide is commercially available in several forms such as anhydrous solution in hydrocarbons and aqueous solution of various concentrations (90% and less) and can be utilized as such without purification. However preferably tert-butyl hydroperoxide is used as a 70% aqueous solution.

Generally, an amount of about 1.5 mole equivalent to about 5.0 mole equivalents of metal hypochlorite, preferably about 2.0 mole equivalents to about 4.0 mole equivalents, and more preferably about 2.5 mole equivalents to about 3.5 mole equivalents per mole equivalent of allylic compound, is most effective for allylically oxidizing an allylic compound.

The amount of tert-butyl hydroperoxide needed for the inventive process is about 2 to 10 mole equivalents of tert-butyl hydroperoxide solution per mole equivalent of allylic compound, preferably about 3 to 8 mole equivalents of tert-butyl hydroperoxide per mole equivalent of allylic compound, and still more preferably about 4 to 6 mole equivalents of tert-butyl hydroperoxide per mole equivalent of allylic compound. Amounts of less than about 1 mole equivalent of hypochlorite oxidant and less than about 2 mole equivalent of tert-butyl hydroperoxide significantly lower the yield of the oxidized product, while greater than ~5 mole equivalents of metal hypochlorite and ~10 mole equivalents of tert-butyl hydroperoxide increase the bulk of the reaction mixture without producing any corresponding increase in any beneficial property or characteristic of the process or resultant product thereof The procedure of the present invention can be carried out without any organic solvent as well as in the presence of a suitable inert organic solvent or a combination of suitable inert organic solvents. However when desired a wide selection of organic solvents, water miscible to water immiscible as well as polar to non-polar solvents or combination thereof can be used to carry out allylic oxidation. The organic reactants (i.e. allylic compound and tert-butyl hydroperoxide) can be conveniently dissolved in conventional organic solvent(s) as defined hereafter, depending upon the specific allylic compound used.

The conventional solvents utilized in the present invention are selected for their inertness towards oxidants as well as industrial viability, low cost, ease of handling, their ability to dissolve the organic reactants and to facilitate reactive contact between the hypochlorite, hydroperoxide and the organic substrate. The organic substrate may be suitably dissolved in a water miscible organic solvent or in a water immiscible organic solvent(s) or a combination thereof, depending upon the nature of the substrate. Conventional organic solvents include specifically, but not exclusively, lower aliphatic esters such as ethyl acetate, lower aliphatic ketones like acetone, lower aliphatic alkyl nitrites like acetonitrile, lower tertiary alcohols like tert-butanol, aliphatic hydrocarbons such as lower n-alkanes, aromatic hydrocarbons, halogenated solvents like dichloroethane, organic bases such as pyridine etc. Mixtures of these solvents can also be used if desired. Lower primary and secondary alcohols and aromatic hydrocarbons substituted with alkyl groups having cc hydrogen(s) are specifically excluded as solvents from the scope of the present invention.

The reaction time can vary depending upon the reaction conditions and is dependent upon a number of variables, more importantly the reaction temperature and the rate of the addition of the hypochlorite solution, the specific allylic compound being oxidized, and the concentration of reactants within the reaction mixture. In a preferred mode of the invention, the reactions can typically be conducted in about 8 to about 14 hours at 5+/−5° C.

The quality and yield of the allylically oxidized product is dependent upon the rate of addition of hypochlorite oxidant. The metal hypochlorite, must be added from outside to the reaction mixture either in the form of an aqueous solution or as a solid. It should be added very slowly during the entire period of the reaction time. The rate of addition of hypochlorite should be so adjusted that it takes about 2–20 hrs preferably about 4–16 hrs and more preferably about 8–14 hrs to complete the addition; the exact rate being dependent upon the nature of the substrate, the reaction temperature, amount of tert-butyl hydroperoxide etc. However it has been observed that fast addition of hypochlorite (less than 6–8 hours) results in lower yield.

The allylic oxidation reaction of the inventive process is generally conducted at sub ambient to ambient temperatures (i.e. temperatures between −5° C. to 25° C.), preferably at −2° to 20° C. and still more preferably at 0–10° C.

The reaction mixture should be continuously and vigorously stirred during the course of the reaction in order to promote efficient contact between the reactants and immediate dispersion of the added hypochlorite solution or solid into the mixture so as to speed-up the reaction and enhance the yield and/or quality of the desired allylically oxidized product.

The optimal pH of the reaction mixture primarily depends upon the specific metal hypochlorite being used. The preferred oxidant of the present invention viz. aqueous sodium hypochlorite is basic (pH~11) and is best utilized at pH 10 to 11, alone or in presence of a buffering agent such as a carbonate. If necessary the reaction mixture can be buffered to a lower pH of 9 by addition of buffering agents such as bicarbonates and carbonates. Solid oxidant such as calcium hypochlorite may be added as such or as an aqueous solution to the reaction mixture.

Phase transfer catalysts such as tetraalkylammonium salts do not affect the course of the reaction. No increase in yield was observed when a phase transfer catalyst such as tetrabutylammonium salt was added to the reaction mixture. However, a phase transfer agent can be added to the reaction mixture for the purpose of dissolving specific substrates into aqueous medium, if desired.

After the completion of the oxidation, alkyl hydroperoxide when still present unreacted and unwanted can be decomposed by methods known to those skilled in the art such as treating the reaction mixture with a sulfite solution.

The desired oxidized product can be separated from the reaction mixture by one or more of the techniques known to those skilled in the art such as extraction, distillation including distillation under high vacuum, crystallization etc. In general the product can be isolated in good yield and purity by separating the organic layer, if immiscible, from the aqueous layer followed by washing the organic layer with water, concentration, precipitation and/or crystallization. An additional small quantity of the product can be claimed from the mother liquor by chromatography if desired.

The following examples including the standard protocol serve to illustrate the allylic oxidation of various organic compounds having at least two allylic hydrogen atoms, employing a metal hypochlorite and an alkyl hydroperoxide. These examples are illustrative of the invented process and are by no means exhaustive.

STANDARD PROTOCOL

An allylic substrate (0.01 mol) was dissolved in an organic solvent (30–60 ml), 70% aqueous solution of tert-butyl hydroperoxide (0.06 mol) was added followed by sodium carbonate (0.002 mol). The reaction mixture was stirred vigorously, cooled to 0–5° C. and aqueous sodium hypochlorite solution (5.25% available chlorine, sold as household bleach, 30–40 ml) was added in the form of fine droplets with the help of a pressure equalizing dropping funnel. This slow addition of aqueous sodium hypochlorite solution was maintained for 10–12 hours at 0–5° C. After completion of addition, the reaction mixture was stirred with sodium sulfite (0.022 mol) at 40–50° C. for 2–4 hours. The aqueous layer was removed, the organic layer was washed with water (2×10 ml), dried and solvent was distilled off under reduced pressure. The crude product was crystallized from alcohol (solids) or chromatographed (liquids) and/or distilled under high vacuum (liquids) to obtain purified allylically oxidized product.

EXAMPLE 1

Oxidation of 3β-acetoxyandrost-5-en-17-one (DHEA-Ac, 2) (at 0–5° C. using aq. sodium hypochlorite) to 3β-acetoxyandrost-5-ene-7,17-dione (3)

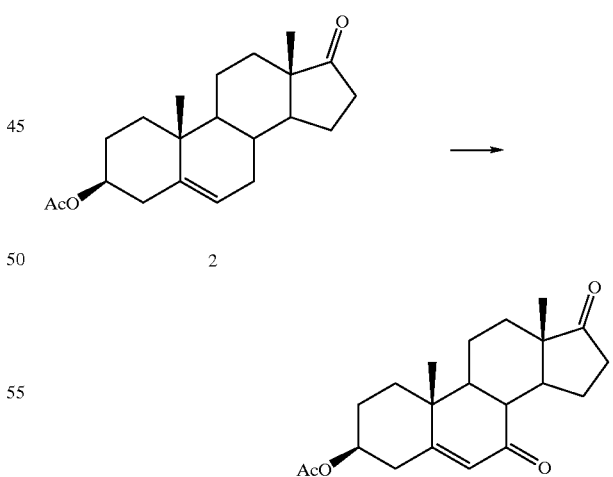

A solution of DHEA-Ac (2, 3.3 gm, 0.01 mol) in ethyl acetate (27 ml) and n-hexane (3 ml) was stirred along with a small amount of sodium bicarbonate (0.2 gm) in a 250 mL three necked flask fitted with a thermometer and a pressure equalizing dropping funnel. An aqueous solution of tert-butyl hydroperoxide (70% aqueous solution from Aldrich, 6.0 ml, 4.5 mol. equivalents) was added and mixture was cooled to 0–5° C. Aqueous sodium hypochlorite solution (30 ml, 5.25% available chlorine) was added very slowly in the form of fine, small droplets under vigorous stirring to the cooled solution during a period of 12 hours.

After completion of addition, the solution was stirred with sodium sulfite (3.0 gm) for 2 hours at 40–45° C. The aqueous yellow layer was separated and the organic layer was washed with half saturated brine, dried over anhydrous magnesium sulfate, and solvent was evaporated on a rotary evaporator. On triturating with methanol, 3β-acetoxyandrost-5-en-7,17-dione (3) crystallized out as a white solid; the mixture was cooled and solid was filtered, weight 1.8 gm. The mother liquor was concentrated and an additional 0.5 gm of product 3 was obtained from methanol. Yield 67% (2.3 gm). Recrystallized from methanol, melting point 184–186° C.

$^1$H NMR (CDCl$_3$, 200 MHz): δ5.75 (1H, d, J=1.4 Hz, 6H), 4.74 (1H, m, 3α-H), 2.06 (3H, s, OCOCH$_3$), 1.24 (3H, s, 19-CH$_3$), 0.89 (3H, s, 18-CH$_3$). $^{13}$C NMR (CDCl$_3$, 200 MHz): δ221.0 (17-C), 200.2 (7-C), 169.8 (CO, acetate), 164.5 (5-C), 126.3 (6-C), 71.8 (3-C), 50.0, 47.7, 45.8, 44.3, 38.4, 37.8, 35.9, 35.4, 30.7, 27.2, 24.0, 21.0 (CH(s), CH$_2$ (s), and quaternary-C), 20.5 (CH$_3$, acetate), 17.3 (19-CH$_3$), 13.6 (18-CH$_3$).

EXAMPLE 2

Oxidation of 3β-acetoxyandrost-5-en-17-one (2) (at 10° C. without solvent) to 3β-acetoxyandrost-5-ene-7,17-dione (3)

DHEA-Ac (2, 3.3 gm, 0.01 mol) and sodium carbonate (0.2 gm) were dissolved in an aqueous solution of tert-butyl hydroperoxide (70% aqueous solution from Aldrich, 10.0 ml, 7.5 mol equivalents) and the solution was stirred vigorously at 10° C. An aqueous sodium hypochlorite solution (30 ml, 5.25% available chlorine) was added very slowly from a pressure equalizing dropping funnel in the form of fine, small droplets to the cooled solution during a period of ten hours.

The mixture was stirred with sodium sulfite (3.0 gm) for 2 hours at 40–45° C, cooled and the product was extracted with ethyl acetate. The organic layer was washed with half saturated brine, dried over anhydrous magnesium sulfate, and evaporated on a rotary evaporator. On triturating with ether, 30-acetoxyandrost-5-en-7,17-dione (3) crystallized out as a white solid when cooled; the solid was filtered by suction, weight 1.75 gm. Concentration of the mother liquor afforded an additional 0.5 gm of crystalline product 3. Yield 65.4% (2.25 gm). The product was recrystallised from methanol. melting point 184–186° C.

EXAMPLE 3

3β-Acetoxyandrost-5-ene-7,17-dione (7-Oxo-DHEA-Ac 3): starting from DHEA (1)

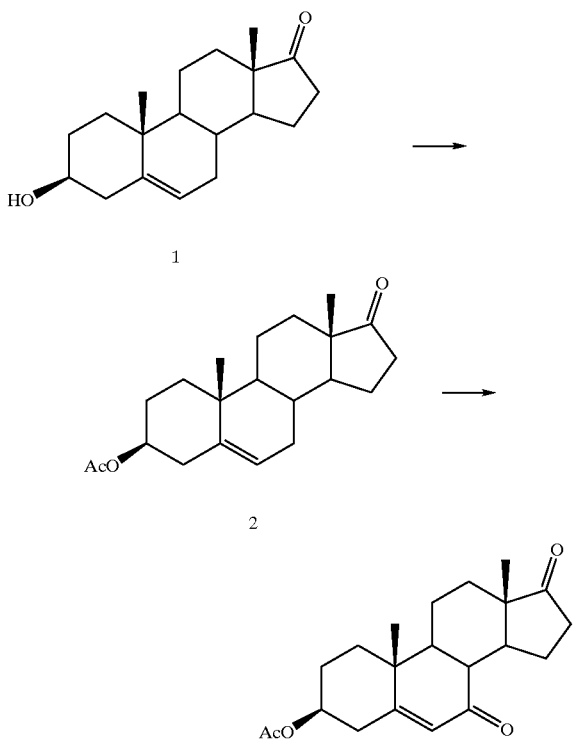

3β-Hydroxyandrost-5-en-17-one (DHEA, 1) (100.0 g, 0.347 mol) was dissolved in a mixture of ethyl acetate (1000.0 ml) and acetic anhydride (60.0 ml 0.63 mol). Freshly dried anhydrous sodium acetate (150.0 gm) was added to the solution and the resulting mixture was refluxed for 12 hours. The mixture was cooled to 10–15° C., water (350 ml) was added and reaction mixture was stirred for 1 hour. The organic layer was separated and stirred with a cold aqueous solution of sodium hydroxide (70 ml of 25% solution, w/v) at 10–15° C. for 1 hour (organic layer was checked for any residual acidity). The aqueous layer was removed and the organic layer containing 3β-acetoxyandrost-5-en-17-one (DHEA-Ac, 2) was washed twice (2×50 ml) with water and used as such for the oxidation.

The above solution of DHEA-Ac (2) in ethyl acetate (~1000 ml) was taken in a 5L three necked flask fitted with a thermometer and a pressure equalizing dropping funnel. An aqueous solution of tert-butyl hydroperoxide (70% aqueous solution from Aldrich, 270 ml, 6.0 equivalents) was added and the mixture was cooled to 0–5° C. Aqueous sodium hypochlorite solution (950 ml, 5.25% solution, purchased as house hold bleach) was added dropwise under good stirring to the cooled solution during a period of ten hours at 0–5° C. After completion of addition, the lower aqueous layer was removed and the organic (ethyl acetate) layer was stirred with sodium sulfite solution (100.0 gm in 300 ml of water) for 3 hours at 40–45° C. The aqueous yellow layer was removed and the organic layer was washed twice with 100 ml of half saturated brine, dried over anhydrous magnesium sulfate and concentrated to 50 ml volume. On triturating with hexane, 3β-acetoxyandrost-5-en-7,17-dione (7-oxo-DHEA-Ac, 3) crystallized out as a white solid, yield 79.4 gm (66.5%, based on DHEA), purity (HPLC) 98.86%. The resulting solid was recrystallized from ethanol, providing 3β-acetoxyandrost-5-en-7,17-dione (3) as white crystalline solid (70.0 gm, purity (HPLC) 99.8%, melting point 185–186° C.

Combined mother liquors were concentrated and taken in 50 ml of methanol. On cooling product 3 was crystallized out which was filtered and dried; an additional 10.0 gm of 7-oxoDHEA-Ac (3) was obtained. Total yield 80.0 gm, 67% based on DHEA.

EXAMPLE 4

Oxidation of 3β-acetoxyandrost-5-en-17-one (DHEA-Ac. 2) (at 10° C. using aq. sodium hypochlorite) to 3β-acetoxyandrost-5-ene-7,17-dione (3)

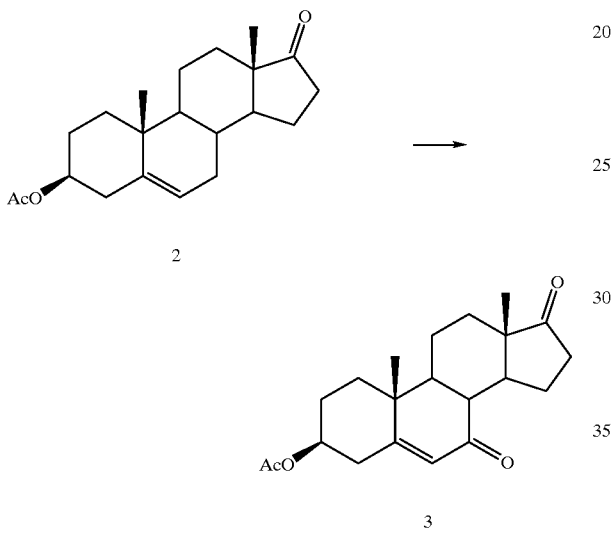

A solution of DHEA-Ac (2, 3.3 gm, 0.01 mol) in ethyl acetate (35 ml) was taken in a 250 mL three necked flask fitted with a thermometer and a pressure equalizing dropping funnel. An aqueous solution of tert-butyl hydroperoxide (70% aqueous solution from Aldrich, 8.0 ml, 6.0 equivalents) was added and mixture was cooled to 10° C. Aqueous sodium hypochlorite solution (30 ml, 5.25% available chlorine) was added very slowly in the form of fine, small droplets under vigorous stirring to the cooled solution during a period of ten hours.

After completion of addition, the lower aqueous layer was removed and the ethyl acetate layer was stirred with sodium sulfite solution (3.0 gm in 10 ml of water) for 3 hours at 40–45° C. The aqueous yellow layer was separated and the organic layer was washed with half saturated brine, dried over anhydrous magnesium sulfate and solvent was evaporated on a rotary evaporator. On triturating with methanol, 3β-acetoxyandrost-5-en-7,17-dione (3) crystallized out as a white solid; it was cooled and solid was filtered under suction, weight 2.2 gm, yield 64%, melting point 185–186° C.

EXAMPLE 5

Oxidation of 3β-acetoxyandrost-5-en-17-one (DHEA-Ac, 2), (using 1,2-dichloroethane and aq. Sodium hypochlorite) to 3β-acetoxyandrost-5-ene-7,17-dione (3).

DHEA-Ac (2, 3.3 gm, 0.01 mol.) in 1,2-dichloroethane (30 ml) was taken in a 250 ml three necked flask fitted with a thermometer and a pressure equalizing dropping funnel. An aqueous solution of tert-butyl hydroperoxide (70% aqueous solution from Aldrich, 3.0 ml, 2.3 equivalents) was added, and mixture was cooled to 0–5° C. Aqueous sodium hypochlorite solution (30 ml, 5.25% available chlorine) was added very slowly in the form of fine, small droplets under cooling (0–5° C.) and good stirring during a period of ten hours. After completion of addition, the aqueous yellow layer was removed, the organic layer was washed with water, dried over anhydrous magnesium sulfate, and the solvent was evaporated on a rotary evaporator. On triturating with methanol, 3β-acetoxyandrost-5-en-7,17-dione (7-oxo-DHEA-Ac, 3) crystallized out as a white solid, weight 1.65 gm.

The mother liquor was found to contain some unreacted starting material (TLC). It was evaporated to dryness and dissolved in 1,2-dichloroethane (20 ml), mixed with tert-butyl hydroperoxide (70% aqueous solution, 2.0 ml), cooled to 0–5° C. and aqueous sodium hypochlorite solution (15 ml, 5.25% solution) was added slowly and drop wise during a period of eight hours.

The lower organic layer was separated and stirred with sodium sulfite solution (3.0 gm in 10 ml of water) for 2 hours at 40–45° C., washed with water, dried and solvent removed. The crude product was crystallized from methanol to afford 0.6 gm of 7-oxo-DHEA-AC (3), melting point 185–186° C. Total yield 2.2 gm, 64%.

EXAMPLE 6

Oxidation of 3β-acetoxyandrost-5-en-17-one (2) (using a mixture of two solvents) to 3β-acetoxyandrost-5-ene-7,17-dione (3)

In a 250 mL three necked flask fitted with a thermometer and a pressure equalizing dropping funnel, DHEA-Ac (2, 3.3 gm., 0.01 mol) was taken into a mixture of ethyl acetate (25 ml) and cyclohexane (6 ml) and cooled to 0–5° C. and an aqueous solution of tert-butyl hydroperoxide (70% aqueous solution from Aldrich, 3.0 ml, 0.023 mol) was added. Aqueous sodium hypochlorite solution (30 ml, 5.25% available chlorine) was added very slowly in the form of fine, small droplets under good stirring to this cooled solution during a period of ten hours at 0–5° C.

The lower aqueous layer was then removed and the organic ethyl acetate layer was stirred with sodium sulfite solution (3.0 gm in 10 ml of water) for 3.5 hours at 40–45° C. The aqueous yellow layer was removed and the organic layer was washed with half saturated brine, dried over anhydrous magnesium sulfate, and the solvent was evaporated on a rotary evaporator. On triturating with methanol, 3β-acetoxyandrost-5-en-7,17-dione (3) crystallized out as a white solid, weight 1.6 gm.

The last remains of the product (3) from the mother liquor were obtained by column chromatography of the mother liquor (adsorbed on silica gel) on a small column of silica gel (80–200 mesh) utilizing hexane-acetone (85:15) as eluent. An additional 0.15 gm of 7-oxo-DHEA-Ac (3) was obtained. Total yield 1.75 gm, 56.5% (based on 90% conversion), melting point 185–186° C.

EXAMPLE 7

Oxidation of 3β-acetoxyandrost-5-en-17-one (2) (using a mixture of two solvents) to 3β-acetoxyandrost-5-ene-7,17-dione (3).

DHEA-Ac (2, 1.0 gm., 0.003 mol.) was dissolved in a mixture of acetone (15 ml) and ethyl acetate (5 ml). An aqueous solution of tert-butyl hydroperoxide (70% aqueous solution from Aldrich, 1.5 ml, 0.011 mol) was added and the mixture was cooled to 0–5° C. Aqueous sodium hypochlorite solution (10 ml, 5.25% available chlorine) was added very slowly in the form of fine, small droplets under good stirring during a period of eight hours at 0–5° C.

The reaction mixture was then concentrated, diluted with ethyl acetate (10 ml) and stirred with sodium sulfite (1.0 gm) for 1 hour at 40–45° C. The aqueous yellow layer was removed and the organic layer was washed with half saturated brine, dried over anhydrous magnesium sulfate, and the solvent was evaporated on a rotary evaporator. On triturating with diethyl ether, 3β-acetoxyandrost-5-en-7,17-dione (3) crystallized out as a white solid, yield 0.75 gm, 72.8%. Recrystallization from methanol afforded 0.62 gm (60%) of pure 7-oxo-DHEA-Ac (3), melting point 184–186° C.

EXAMPLE 8

Oxidation of 3β-acetoxyandrost-5-en-17-one (DHEA-Ac, 2) (at room temperature and in a mixture of two solvents) to 3β-acetoxyandrost-5-ene-7,17-dione (3).

In a 100 mL three necked flask fitted with a thermometer and a pressure equalizing dropping funnel, DHEA-Ac (1.0 gm., 0.003 mol.) was taken along with a mixture of tert-butanol (10 ml) and ethyl acetate (3 ml). An aqueous solution of tert-butyl hydroperoxide (70% aqueous solution from Aldrich, 1.5 ml, 0.011 mol) was added and the mixture was stirred at room temperature. Aqueous sodium hypochlorite solution (10 ml, 5.25% available chlorine) was added very slowly in the form of fine small droplets under good stirring during a period of seven hours.

The reaction mixture was then diluted with water and ethyl acetate, and the lower aqueous layer was removed. The organic layer was stirred with sodium sulfite solution (3.0 gm in 10 ml of water) for 1 hour at 40–45° C. The aqueous yellow layer was removed and the organic layer was washed with half saturated brine, dried over anhydrous magnesium sulfate, and the solvent was evaporated on a rotary evaporator. On triturating with diethyl ether, 3β-acetoxyandrost-5-en-7,17-dione (3) crystallized out as a white solid, weight 0.55 gm, 53.4% (low yield due to room temperature reaction and fast addition of hypochlorite), melting point 183–185° C.

EXAMPLE 9

Oxidation of 3β-acetoxyandrost-5-en-17-one (2) (using dichloromethane and aq. sodium hypochlorite) to 3β-acetoxyandrost-5-ene-7,17-dione (3).

DHEA-Ac (2, 1.1 gm., 0.0033 mol.) was dissolved in dichloromethane (7 ml), tert-butyl hydroperoxide (70% aqueous solution from Aldrich, 3.0 ml, 0.023 mole) was added, and mixture was cooled to 0–5° C. Aqueous sodium hypochlorite solution (10 ml, 5.25% available chlorine) was added very slowly in the form of fine, small droplets under good stirring during a period of ten hours at 0–5° C.

The lower organic layer was then separated and stirred with sodium sulfite solution (3.0 gm in 10 ml of water) for 3 hours at 40–45° C. The aqueous yellow layer was removed and the organic layer was washed with half saturated brine, dried over anhydrous magnesium sulfate and the solvent was evaporated on a rotary evaporator. On triturating with methanol, 3β-acetoxyandrost-5-en-7,17-dione (3) crystallized out as a white solid, weight 0.77 gm, yield 73.6%.

EXAMPLE 10

Oxidation of 3β-acetoxyandrost-5-en-17-one (2) (using 1,2-dichloroethane and calcium hypochlorite at room temperature) to 3β-acetoxyandrost-5-ene-7,17-dione (3)

DHEA-Ac (2, 1.1 gm., 0.0033 mol.) was dissolved in a mixture of 1,2-dichloroethane (10 ml) and tert-butyl hydroperoxide (70% aqueous solution from Aldrich, 3.0 ml, 0.023 mol). The mixture was stirred at room temperature and solid calcium hypochlorite (0.65 gm.) was added in very small portions over a period of seven hours. The aqueous layer was then separated and the organic layer was stirred with sodium sulfite solution (3.0 gm in 10 ml of water) for 3 hours at 40–45° C. and filtered over a small bed of celite. The aqueous yellow layer was removed and the organic layer was washed with half saturated brine, dried over anhydrous magnesium sulfate, and the solvent was evaporated on a rotary evaporator. The crude product was crystallized from methanol, afforded 3β-acetoxyandrost-5-en-7,17-dione (3) as a white solid, weight 0.38 gm.

The mother liquor was filtered through a small column of silica gel (80–200 mesh) utilizing hexane-acetone (85:15) as eluent. An additional 0.2 gm of 7-oxo-DHEA-Ac (3) was obtained. Total yield 0.58 gm, 50.8%.

EXAMPLE 11

Oxidation of 3β-acetoxyandrost-5-en-17-one (2) (using ethyl acetate and calcium hypochlorite at 10° C.) to 3β-acetoxyandrost-5-ene-7,17-dione (3)

DHEA-Ac (1.1 gm., 0.0033 mol.) was dissolved in a mixture of ethyl acetate (10 ml) and tert-butyl hydroperoxide (70% aqueous solution from Aldrich, 2.0 ml, 0.015 mol). The mixture was stirred at 10° C. and solid calcium hypochlorite (0.65 gm.) was added in small portions during a period of seven hours. The aqueous layer was then separated and the organic layer was stirred with sodium sulfite solution (3.0 gm in 10 ml of water) for 3 hours at 40–45° C. and filtered over celite. The aqueous yellow layer was removed and the organic layer was washed with half saturated brine, dried over anhydrous magnesium sulfate, and the solvent was evaporated on a rotary evaporator. The crude product, crystallized from methanol, afforded 3β-acetoxyandrost-5-en-7,17-dione (3) as a white solid, weight 0.42 gm.

The mother liquor was filtered through a small column of silica gel (80–200 mesh) utilizing hexane-acetone (85:15) as eluent. An additional 0.22 gm of 7-oxo-DHEA-Ac (3) was obtained, melting point 185–186° C., total yield 0.64 gm, 56%.

EXAMPLE 12

Oxidation of 3β-acetoxyandrost-5-en-17-one (2) (using 10–13% aq. sodium hypochlorite) to 3β-acetoxyandrost-5-ene-7,17-dione (3)

DHEA-Ac (2, 5.7 gm., 0.017 mol.) was dissolved in a mixture of ethyl acetate (50 ml) and tert-butyl hydroperoxide (70% aqueous solution from Aldrich, 14.0 ml, 6 mol equivalents) and the solution was cooled to 0–5° C. Aqueous sodium hypochlorite solution (20 ml, 10–13% solution obtain from Aldrich) was added very slowly in the form of fine, small droplets under good stirring and cooling (0–5° C.) during a period of ten hours.

The lower aqueous layer was then removed and the organic (ethyl acetate) layer was stirred with sodium sulfite solution (5.0 gm in 15 ml of water) for 24 hours at room temperature. The aqueous yellow layer was separated and the organic layer was washed with half saturated brine, dried over anhydrous magnesium sulfate, and the solvent was concentrated to about 5 ml volume on a rotary evaporator. On triturating with cold petroleum-ether, 3β-acetoxyandrost-5-en-7,17-dione (3) crystallized out as a white solid, weight 3.5 gm.

The mother liquor was concentrated and an additional 0.3 gm of 7-oxo-DHEA-Ac (3) was crystallized from methanol. Combined yield 3.8 gm, 64.9%, melting point 184–186° C. (methanol).

EXAMPLE 13

Oxidation of 3β-acetoxyandrost-5-en-17-one (2) (using 10 equivalents of tert-butyl hydroperoxide) to 3β-acetoxyandrost-5-ene-7,17-dione (3)

DHEA-Ac (2, 5.7 gm., 0.0173 mol.) was dissolved in a mixture of ethyl acetate (50 ml) and tert-butyl hydroperoxide (70% aqueous solution from Aldrich, 22.0 ml, 0.17 mol). The mixture was cooled to 0–5° C. and aqueous solution of sodium hypochlorite (50 ml, 5.25% available chlorine) was added very slowly during ten hours.

The organic layer was then separated and stirred with sodium sulfite solution (5.0 gm in 15 ml of water) for 3 hours at 40–45° C. The aqueous yellow layer was removed and the organic layer was washed with half saturated brine, dried over anhydrous magnesium sulfate, and the solvent was evaporated on a rotary evaporator. The crude product was crystallized from methanol to afford 3β-acetoxyandrost-5-en-7,17-dione (3) as a white solid, weight 3.6 gm.

The mother liquor was concentrated and an additional 0.5 gm of 7-oxo-DHEA-Ac was crystallized from methanol. Combined yield 4.1 gm, 68.9%, melting point 184–186° C.

EXAMPLE 14

Oxidation of 3β-acetoxyandrost-5-en-17one (2) (using pyridine) to 3β-acetoxyandrost-5-ene-7,17-dione (3)

A clear solution of DHEA-Ac (2, 3.3 gm., 0.01 mol.) in a mixture of pyridine (25 ml) and tert-butyl hydroperoxide (70% aqueous solution from Aldrich, 8.0 ml, 0.06 mol) was cooled to 0–5° C. Aqueous sodium hypochlorite solution (30 ml, 5.25% available chlorine) was added very slowly in the form of fine, small droplets under good stirring to the cooled solution during a period of ten hours at 0–5° C.

The reaction mixture was diluted with water and extracted with ethyl acetate. The organic layer was washed twice with water, dried over anhydrous magnesium sulfate, and the solvent was concentrated to about 5 ml on a rotary evaporator. On trituration with petroleum-ether the product 3 was obtained as white solid. Crystallization from methanol afforded 3β-acetoxyandrost-5-en-7,17-dione (3) as a white pure solid, weight 1.6 gm.

The mother liquor was concentrated and the residue was taken in ether and the solution was cooled for 1 h at 0–5° C. An additional 0.4 gm of 7-oxo-DHEA-Ac (3) was obtained. Total yield 2.0 gm, 64.6% (based on 90% conversion), melting point 183–185° C.

EXAMPLE 15

Oxidation of 3β-hydroxyandrost-5-en-17-one (DHEA 1) to 3β-hydroxyandrost-5-ene-7,17-dione (7-Oxo-DHEA 4)

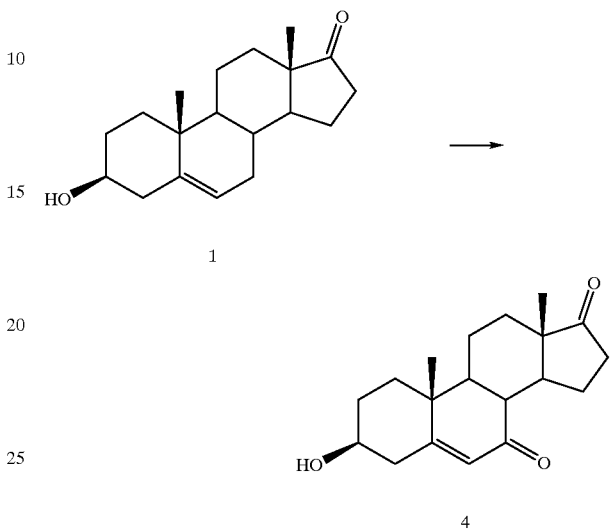

3β-Hydroxyandrost-5-en-17-one (DHEA, 1, 2.88 g, 0.01 mol) and aqueous tert-butyl hydroperoxide (70% solution, 8.3 ml, 0.06 mol) were taken in ethyl acetate (50 ml). The mixture was cooled to 0–5° C., stirred vigorously and aqueous sodium hypochlorite solution (5.25% available chlorine, 30 ml) was added slowly and dropwise during a period often hours at 0–5° C.

After removing the lower aqueous layer, the organic layer was stirred with sodium sulfite solution (3 gm in 10 ml of water) at room temperature for 1 hour. The organic layer was washed twice with water, dried over anhydrous magnesium sulfate, and concentrated on a rotary evaporator to about 5 ml volume. The product 3β-hydroxyandrost-5-en-7,17-dione (7-oxo-DHEA, 4) crystallized out upon addition of diethyl ether to the concentrate. It was cooled at 0–5° C. for 2 hours and filtered under suction to give 1.92 gm product. Another 0.2 gm of the desired product was obtained by evaporating the mother liquor under vacuum, and crystallizing from methanol; yield 2.12 gm, 70.2%.

The solid was recrystallized from acetone-hexane to yield 2.05 g (67.9%) of white crystalline 3β-hydroxyandrost-5-en-7,17-dione (7-oxo-DHEA, 4) having a melting point of 234–236° C.

$^1$H NMR (CDCl$_3$, 200 MHz): δ5.75 (1H, d, J=1.47 Hz, 6H), 3.7 (1H, m, 3α-H), 1.23 (3H, s, 19-CH$_3$), 0.9 (3H, s, 18-CH$_3$). $^{13}$C NMR (CDCl$_3$, 200 MHz): δ219.8 (17-C) 200.7 (7-C), 166.2 (5-C), 125.7 (6-C), 70.2 (3-C), 50.3, 47.8, 45.9, 44.4, 41.9, 38.4, 36.4, 35.5, 31.1, 30.8, 24.1, 21.6 (CH(s), CH$_2$ (s), and quaternary-C), 17.4 (19-CH$_3$), 13.7 (18-CH$_3$).

EXAMPLE 16

Oxidation of 3,3-ethylenedioxy-17β-acetoxyandrost-5-ene (5) to 3.3-ethylenedioxy-17β-acetoxyandrost-5-en-7-one (6)

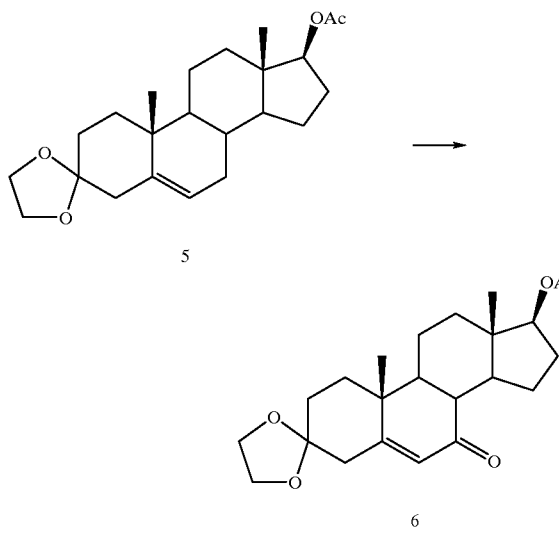

3,3-Ethylenedioxy-17β-acetoxyandrost-5-ene (5, 0.748 gram, 0.002 mol) and aqueous tert-butyl hydroperoxide (70% solution, 1.7 ml) were dissolved in ethyl acetate (20 ml). The clear solution was cooled to 0–5° C., stirred vigorously and a dilute aqueous solution of sodium hypochlorite (5.25% available chlorine, 6 ml) was added dropwise during a period often hours at 0–5° C.

The organic layer was separated, washed with sodium sulfite and water, dried over magnesium sulfate, and the solvent was removed on a rotary evaporator to yield a crude material. The crude solid was crystallized from methanol to afford 0.49 gm of 3,3-ethylenedioxy-17β-acetoxyandrost-5-en-7-one (6) as a white crystalline solid. The mother liquor was concentrated and an additional 0.058 gm of pure product, 6 was obtained from ethyl acetate-petroleum ether. Yield 0.548 gm (70.6%), m. p. 252–54° C. (acetone-hexane).

$^1$H NMR (CDCl$_3$, 200 MHz): δ5.68 (1H, d, J=1.71 Hz, 6H), 4.63 (1H, dd, J=6.83, 9.53, 17α-H), 3.97 (4H, m, O—CH$_2$—CH$_2$—O), 2.05 (3H, s, OCOCH$_3$), 1.21 (3H, s, 19-CH$_3$), 0.82 (3H, s, 18-CH$_3$).

The above reaction was also carried out using dichloromethane as solvent in place of ethyl acetate under same reaction conditions as described above, and the same product and similar yield was obtained.

EXAMPLE 17

Oxidation of 3,3,17,17-diethylenedioxyandrost-5-ene (7) to 3,3,17,17-diethylenedioxyandrost-5-en-7-one (8)

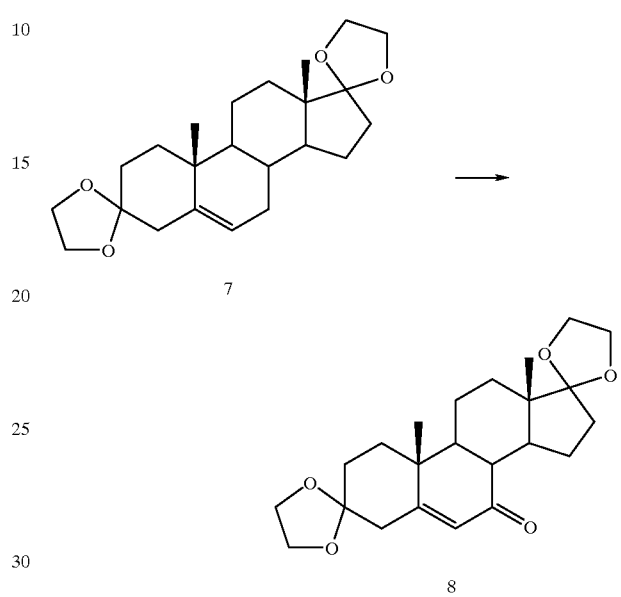

3,3,17,17-Diethylenedioxyandrost-5-ene (7, 2.0 gm, 0.005 mol) and aqueous tert-butyl hydroperoxide (70% solution, 7.0 ml, 10 equivalents) were dissolved in ethyl acetate (80 ml). The clear solution was cooled to 0–5° C., stirred vigorously, and a dilute aqueous solution of sodium hypochlorite (5.25% available chlorine, 20.0 ml, purchased as household bleach) was added dropwise during ten hours at 0–5° C.

After completion of addition, the organic layer was separated, washed with sodium sulfite and water, dried over magnesium sulfate, and the solvent removed by rotary evaporator to yield a crude material, which was taken in a mixture of diethyl ether and petroleum ether and cooled to afford 3,3,17,17-diethylenedioxyandrost-5-en-7-one (8). Recrystallization from methanol afforded pure 3,3,17,17-diethylenedioxyandrost-5-en-7-one as a white crystalline solid (1.0 gm). The mother liquor was concentrated and crystallized from acetone-petroleum ether to afford an additional 0.2 gm of pure product. Yield 1.2 gm (58.5%), m.p. 200–201° C. (aq. methanol).

$^1$H NMR (CDCl$_3$, 200 MHz): δ5.66 (1H, d, J=1.95 Hz, 6H), 3.96 (4H, m, O—CH$_2$—CH$_2$—O), 3.89 (4H, m, O—CH$_2$—CH$_2$—O), 1.21 (3H, s, 19-CH$_3$), 0.87 (3H, s, 18-CH$_3$)

EXAMPLE 18

Oxidation of testosterone- 17β-acetate to 17β-acetoxyandrost-4-ene-3 6-dione

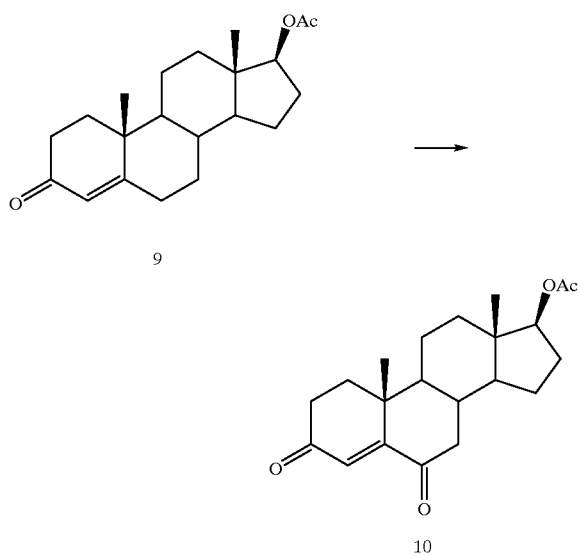

Testosterone acetate (9, 1.65 gm, 0.005 mol) and aqueous tert-butyl hydroperoxide (70% solution, 4.1 ml, 6 equivalents) were dissolved in ethyl acetate (15 ml). The clear solution was cooled to 0–5° C., stirred vigorously and an aqueous solution of sodium hypochlorite (5.25% available chlorine, 15 ml, purchased as household bleach) was added dropwise during a period of ten hours at 0–5° C.

The organic layer was separated, washed with sodium sulfite and water, dried over magnesium sulfate, and the solvent was removed by rotary evaporator to form a crude material. The crude solid was chromatographed on silica gel using acetone-petroleum ether (15:85) as eluent to afford first the starting material, testosterone acetate (0.35 gm) followed by the oxidized product 17β-acetoxyandrost-4-ene-3,6-dione (10, 0.75 gm). Pure product yield 55.5% based on 80% conversion.

$^1$H NMR (CDCl$_3$, 200 MHz): δ6.18 (1H, d, J=0.73 Hz, 4H), 4.64 (1H, dd, J=7.57, 9.28 17α-H), 2.06 (3H, s, OCOCH$_3$), 1.18 (3H, s, 19-CH$_3$), 0.85 (3H, s, 18-CH$_3$).

EXAMPLE 19

Oxidation of 3β-acetoxycholest-5-ene (11) to 3β-acetoxycholest-5-en-7-one (7-Oxo-Cholesteryl-Ac 12)

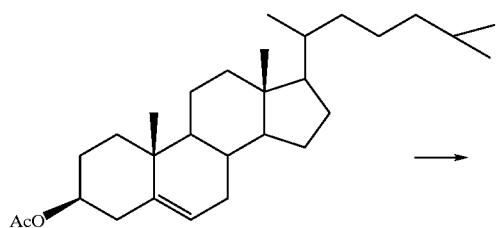

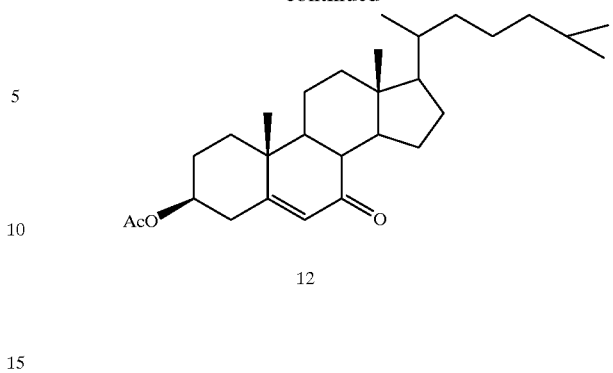

Cholesteryl acetate (11, 2.14 grams, 0.005 mol) and tert-butyl hydroperoxide (4.2 ml of 70% aqueous solution, 0.03 mol) were dissolved in dichloromethane (30 ml). The mixture was stirred vigorously, cooled to 0–5° C. and a dilute solution of sodium hypochlorite (15 ml, 5.25% available chlorine) was added slowly in the form of fine, small drops during a period of ten hours at 0–5° C. The dichloromethane layer was then separated, washed with water, aqueous sodium bisulfite solution (10%, 2×10 ml) and water. The organic solvent was evaporated under reduced pressure and the crude product was recrystallized from methanol. The crystalline material was collected under suction, washed with cold methanol, and dried to yield 1.35 gm of 7-oxo-cholesteryl acetate (12) having a melting point of 155–156 ° C.

$^1$H NMR (CDCl$_3$, 200 MHz): δ5.69 (1H, d, J=1.0 Hz, 6H), 4.72 (1H, m, 3α-H), 2.05 (3H, s, OCOCH$_3$), 1.21 (3H, s, 19-CH$_3$), 0.91 (3H, d, J=6.9 Hz, 21-CH$_3$), 0.88, 0.84 (6H, 2xs, 26,27-CH$_3$), 0.68 (3H, s, 18-CH$_3$).

In order to recover the last remains of the product 12, the mother liquor was chromatographed on silica gel column utilizing 15% acetone in petroleum-ether and 0.15 gm of 7-oxo-cholesteryl acetate (12) was obtained. Total yield of the product 12 was 1.5 gm, 68%.

EXAMPLE 20

Oxidation of 3β-hydoxycholest-5-ene (Cholesterol, 13) to 3β-hydoxycholest-5-en-7-one (7-Oxo-Cholesterol, 14)

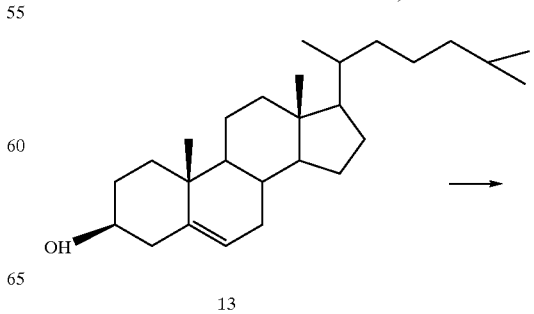

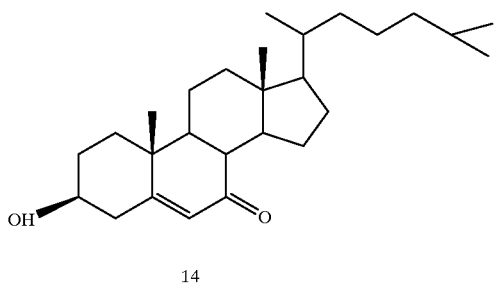

14

Cholesterol (13, 1.93 gm, 0.005 mol) and tert-butyl hydroperoxide (4.2 ml of 70% aq. solution, 0.03 mol) were dissolved in dichloromethane (20 ml). The mixture was stirred vigorously, cooled to 0–5° C. and a dilute solution of sodium hypochlorite (15 ml, 5.25% available chlorine) was added slowly in the form of fine, small droplets during ten hours at 0–5° C. After completion of addition, the dichloromethane layer was separated, washed with water, aqueous sodium bisulfite solution (10%, 2×10 ml) and water. The organic solvent was evaporated under reduced pressure to yield a crude product, which was chromatographed on a silica gel column utilizing 20% acetone in petroleum-ether to afford 1.35 gm (67.5%) of 7-oxo-cholesterol (14) as a snow white solid having a melting point of 169–70° C.

$^1$H NMR (CDCl$_3$, 200 MHz) δ5.68 (1H, d, J=1.46 Hz, 6H), 3.67 (1H, m, 3α-H), 1.20 (3H, s, 19-CH$_3$), 0.91 (3H, d, J=6.6 Hz, 21-CH$_3$), 0.87, 0.84 (6H, 2xs, 26,27-CH$_3$), 0.68 (3H, s, 18-CH$_3$).

EXAMPLE 21

Oxidation of androst-5-ene-3β,17β-diol diacetate (15) (at 0–5° C.) to 3β,17β-diacetoxyandrost-5-en-7-one (16)

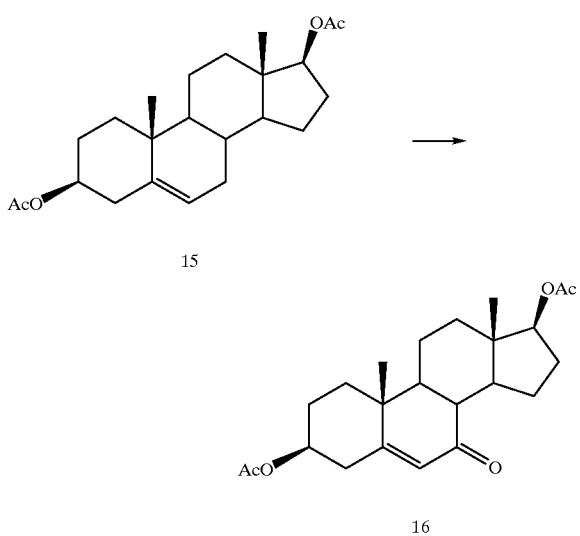

Androst-5-ene-3β,17β-diol diacetate (11.22 gm, 0.03 mol), ethyl acetate (200 ml), petroleum ether (20 ml), sodium carbonate (1.0 gm), and tert-butyl hydroperoxide (70% aqueous solution from Aldrich, 20.0 ml) were mixed together and the solution was stirred vigorously at 0–5° C. A commercially available aqueous sodium hypochlorite solution (100 ml, 5.25% available chlorine) was added very slowly from a pressure equalizing dropping funnel in the form of fine, small droplets to the cooled solution during ten hours.

After completion of addition of hypochlorite, the reaction mixture was stirred with sodium sulfite (10.0 gm) for 2 hours at 50–55° C., cooled and the lower aqueous layer was removed. The organic ethyl acetate layer was washed with half saturated brine, dried over anhydrous magnesium sulfate, and evaporated to about 10 ml volume. On triturating with ether, 3β,17β-diacetoxyandrost-5-en-7-one crystallized out as a white solid, which was cooled and filtered to give 6.67 gm of product. Concentration and crystallization of the mother liquor afforded an additional 0.86 gm of the product, yield 64.7% (7.53 gm). The product was recrystallized from methanol; melting point 222–224° C.

$^1$H NMR (CDCl$_3$, 200 MHz): δ5.72 (1H, d, J=1.4 Hz, 6-H), 4.68 (2H, m, 3α-H and 17α-H), 2.05 (3H, s OCOCH$_3$), 2.045 (3H, s, OCOCH$_3$), 1.21 (3H, s, 19-CH$_3$), 0.80 (3H, s, 18-CH$_3$).

EXAMPLE 22

Oxidation of Fluorene (17) to Fluorenone (18)

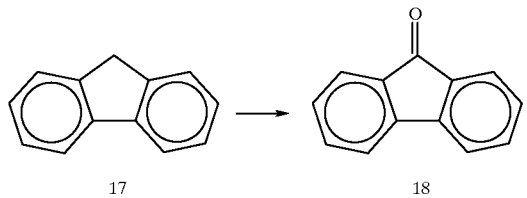

Fluorene (17, 1.66 grams, 0.01 mol) and tert-butyl hydroperoxide (8.2 ml of 70% solution, 0.06 mol) were dissolved in ethyl acetate (30 ml). The mixture was stirred vigorously, cooled to 0–5° C. and a dilute solution of sodium hypochlorite (30 ml, 5.25% available chlorine) was added slowly in the form of fine small droplets during a period of ten hours at 0–5° C. The ethyl acetate layer was separated, washed with water, aqueous sodium bisulfite solution (10%, 2×10 ml) and water. The solution was concentrated under reduced pressure and triturated with cold petroleum ether to afford the yellow product which was recrystallized from methanol to give fluorenone (18) as a yellow crystalline material having a melting point of 82–84° C. (Lit. (Aldrich catalogue) m.p. 82–85° C.). Yield 1.73 gm (96.1%).

$^1$H NMR (CDCl$_3$, 200 MHz): δ7.68 (t), 7.64 (t), 7.5 (m) (8H, ArH).

EXAMPLE 23

Oxidation of acenaphthene to acenaphthenequinone

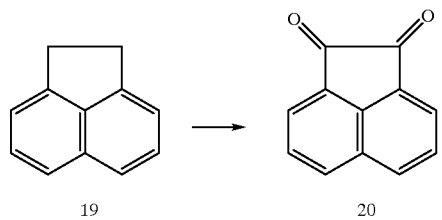

Acenaphthene (19, 1.54 gm, 0.01 mol) and tert-butyl hydroperoxide (8.2 ml of 70% solution, 0.06 mol) were dissolved in ethyl acetate (30 ml). The mixture was stirred vigorously, cooled to 0–5° C. and a dilute solution of sodium hypochlorite (30 ml, 5.25% available chlorine) was added slowly in the form of fine, small droplets during a period of ten hours at 0–5° C. The ethyl acetate layer was then separated, washed with water, aqueous sodium bisulfite solution (10%, 2×10 ml), and water. The solution was concentrated under reduced pressure and triturated with methanol to afford a light yellow product. The product acenaphthenequinone (20) was recrystallized from methanol. Yield 1.24 gm (68%), melting point 250–52° C. (dec.) (Lit.: Aldrich Catalogue m.p. 249–252 ° C. (dec.).

$^1$H NMR (CDCl$_3$, 200 MHz): δ8.64 (2H, dd, J=0.98, 7.33 Hz, ArH), 8.33 (2H, dd, J=0.98, 8.33 Hz, ArH), 7.83 (2H, dd, J=1.0, 7.33 Hz, ArH).

EXAMPLE 24

Oxidation of Diphenylmethane to Benzophenone

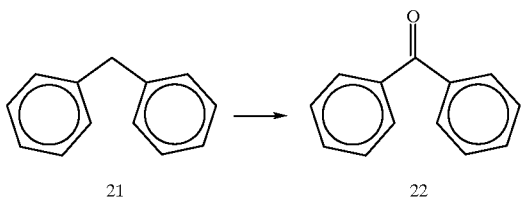

21          22

Diphenylmethane (21, 1.68 grams, 0.01 mol) and tert-butyl hydroperoxide (8.3 ml of 70% aq. solution, 0.06 mol) were dissolved in ethyl acetate (30 ml). The mixture was stirred vigorously, cooled to 0–5° C. and a dilute solution of sodium hypochlorite (30 ml, 5.25% available chlorine) was added slowly in the form of fine, small drops during a period often hours at 0–5° C. The organic solvent layer was separated, washed with water, aqueous sodium bisulfite solution (10%, 2×10 ml) and water. The solvent was evaporated under reduced pressure to yield a crude product. Benzophenone (22) was obtained as white oil (1.78 gm, 97.8% yield) by chromatography of the crude product on silica gel using 5% ethyl acetate-hexane as eluent. The oil solidified on cooling in refrigerator m.p. 47–48° C. (Aldrich Catalogue 48–49° C.).

$^1$H NMR (CDCl$_3$, 200 MWz): δ7.43–7.64 and 7.78–7.83 (10H, m, ArH).

We claim:

1. A process for effecting the allylic oxidation of an allylic compound having at least two allylic hydrogen atoms on the same carbon atom into corresponding α,β-unsaturated carbonyl compound, consisting of oxidizing said allylic compound in a mixture consisting of allylic compound to be oxidized, and an alkyl hydroperoxide in an inert organic solvent system and/or water, by addition of a metal hypochlorite at a temperature of about –5° C. to +25° C.

2. The process of claim 1 wherein said metal hypochlorite is added to the reaction mixture slowly and evenly with continuous stirring during the reaction period.

3. The process of claim 1 wherein said metal hypochlorite is selected from a group consisting of hypochlorites of monovalent alkali metals and divalent metals.

4. The process of claim 3 wherein said metal hypochlorite is an aqueous solution of sodium hypochlorite.

5. The process of claim 1 wherein said alkyl hydroperoxide is tert-butyl hydroperoxide.

6. The process of claim 1 wherein said inert organic solvent system consists of an organic solvent system consisting of one or more organic solvent(s) which are inert to metal hypochlorite, alkyl hydroperoxide and allylic compound under the reaction conditions as described in claim 1.

7. A process according to claim 6 wherein said inert organic solvent system comprises of an alkyl alkanoate, an alkyl nitrite, an alkanone, an alkane, a halogenated hydrocarbon or a tertiary alkanol with a maximum of eight carbon atoms or a mixture thereof.

8. A process according to claim 7 wherein said inert organic solvents are selected from a group consisting of ethyl acetate, acetonitrile, acetone, hexane, 1,2-dichloroethane and tert-butanol or a mixture thereof.

9. The process of claim 1 wherein said allylic compound is a benzylic compound having at least two allylic hydrogen atoms on the same carbon atom.

10. The process of claim 1 wherein said allylic compound is a steroid having at least two allylic hydrogen atoms on the same carbon atom.

11. The process of claim 10 wherein said steroid is a steroid having at least two allylic hydrogen atoms on the same carbon atom.

12. The process of claim 10 wherein said steroid is an androstene having at least two allylic hydrogen atoms on the same carbon atom.

13. The process of claim 12 wherein said androstene is a Δ$^5$-androstene having at least two allylic hydrogen atoms on the same carbon atom.

14. The process of claim 13 wherein said Δ$^5$-androstene is dehydroepiandrosterone or its derivative thereof having at least two allylic hydrogen atoms on the same carbon atom.

15. A process for effecting the allylic oxidation of an allylic compound having at least two allylic hydrogen atoms on the same carbon atom into corresponding α,β-unsaturated carbonyl compound, consisting of oxidizing said allylic compound in a mixture consisting of allylic compound to be oxidized, and tert-butyl hydroperoxide in an inert organic solvent system and/or water, by slow and steady addition of an aqueous solution of sodium hypochlorite with continuous stirring during the reaction period while maintaining the temperature of the reaction mixture at about 0° C. to 10° C.

16. The process of claim 15 wherein said inert organic solvent system is selected from a group consisting of ethyl acetate, acetonitrile, acetone, hexane, 1,2-dichloroethane or tert-butanol or a combination thereof.

17. The process of claim 15 wherein said allylic compound is a steroid having at least two allylic hydrogen atoms.

18. The process of claim 17 wherein said steroid is a steroid having at least two allylic hydrogen atoms on the same carbon atom.

19. The process of claim 17 wherein said steroid is a Δ$^5$-androstene having at least two allylic hydrogen atoms on the same carbon atom.

20. The process of claim 19 wherein said Δ$^5$-androstene is dehydroepiandrosterone or its derivative thereof having at least two allylic hydrogen atoms on the same carbon atom.

* * * * *